United States Patent [19]

Perlman

[11] Patent Number: 5,221,533
[45] Date of Patent: Jun. 22, 1993

[54] SKIN LOTION COMPOSITION

[76] Inventor: H. Harris Perlman, Rittenhouse Claridge - 201 S. 18th S. - Suite 315, Philadelphia, Pa. 19103

[21] Appl. No.: 828,631

[22] Filed: Jan. 31, 1992

[51] Int. Cl.$^5$ .......................... A61K 7/15; A61K 7/26; A61K 7/48
[52] U.S. Cl. .................................. 424/73; 424/195.1; 514/844; 514/847; 514/852; 514/859; 514/861; 514/863; 514/864; 514/873
[58] Field of Search .......................... 514/847; 424/73

[56] References Cited

U.S. PATENT DOCUMENTS 4,994,497  2/1991  Pepper .............................. 514/887

Primary Examiner—Dale R. Ore
Attorney, Agent, or Firm—Caesar, Rivise, Bernstein, Cohen & Pokotilow, Ltd.

[57] ABSTRACT

A skin lotion and methods of use involving a skin lotion comprising effective amounts of allantoin, castor oil, oleic acid, calcium hydroxide powder and witch hazel water. The methods of use include as a keratoplastic and keratolytic for removing the "piled up" hyperkeratotic scales in seborrheic capitis and psoriasis vulgaris; to expedite the involution of the lesions of acute herpes simplex.

3 Claims, No Drawings

SKIN LOTION COMPOSITION

BACKGROUND OF THE INVENTION

This invention relates to a novel and highly useful skin lotion and various methods that can be carried out using such skin lotion.

The present invention involves certain therapeutic uses of the novel skin lotion, as well as a moisturizing use.

The therapeutic uses (which shall be referred to as "therapeutic uses") are as follows:

1. As a keratoplastic and keratolytic for removing the "piled up" hyperkeratotic scales in seborrheic capitis and psoriasis vulgaris.
2. To expedite the involution of the lesions of acute herpes simplex.

The novel lotion of the present invention can also be used as a moisturizer prior to shaving in order to enhance the smoothness of the skin.

All of the foregoing relate to treatment of the skin of a human being.

The prior art known to the inventor shows one or more, but certainly not all of the ingredients of the novel lotion of the present invention. Such prior art includes U.S. Pat. Nos. 4,595,586; 4,459,285; 3,867,528; 3,265,571; 4,512,978; 4,564,462; 4,165,385; 3,062,721; 3,949,071; 4,482,537; 4,295,985; 2,507,236 and 3,987,775.

The novel skin lotion of the present invention in its preferred form comprises the following:

| Ingredient | Amount |
| --- | --- |
| Menthol USP | 24 Gm |
| Allantoin | 120 Gm |
| Glycerin | 250 ml |
| Castor Oil | 250 ml |
| Oleic Acid | 100 ml |
| Span 80 | 120 ml |
| Span 85 | 120 ml |
| Tween 80 | 120 ml |
| Span 40 | 120 Gm |
| Sodium thiosulfate USP | 48 Gm |
| Tragacanth | 88 Gm |
| Ca Hydroxide Powder (Lilly No. 40) | 11.5 Gm |
| Witch Hazel Water | 4000 ml |

The preferred lotion is formulated by mixing the glycerin, castor oil, oleic acid, Span 80, Span 85 and Tween 80 at room temperature. The calcium hydroxide powder (Lilly No. 40) and witch hazel water are then added and shaken until a homogeneous emulsion results.

Then, the menthol, allantoin, and Span 40 are added in s mortar and triturate until a smooth texture is obtained. The tragacanth is then added. A small portion of the emulsion is added to the powdered ingredient, and triturate thoroughly until a smooth homogenous emulsion is achieved. Thorough shaking is continued from time to time until all of the tragacanth has been dissolved, followed by straining through a mesh sieve.

Details of the aforesaid ingredients will now be stated:

MENTHOL U.S.P.

Is a mild rubefacient in the strength contained in the lotion. The cooling effect obtained from menthol contained in the lotion is very much liked from its application to the skin by both sexes.

ALLANTOIN

Is a product of purine metabolism like other ingredients, contained in the lotion, its use in the formula is to increase the emollient effect of the lotion.

GLYCERIN U.S.P

Is an emollient the dehydrating effect of glycerin prevents growth of bacteria. Addition to the other ingredients it serves as an excellent suspending medium in the lotion.

CASTOR OIL

The principal glyceride of castor oil is rincinolein. The fatty acid component is rincinoleic acid. It is a bland emollient softening the skin. Castor oil has been used to remove irritating substances from the eye.

Castor oil does not become rancid because of rincinolein, it aids the penetration of the other ingredients the lotion to overcome the barrier of the stratum corneum, thus, permitting the ingredients to enter the corium. This action may serve to explain the effect on the hair located in the deeper structure of the corium (dermis).

OLEIC ACID

In an unsaturated fatty acid by adding calcium hydroxide powder (Lilly No. 40) to the specific amount of oleic acid contained in the lotion a calcium oleate type of emulsion follows (W/O) with the addition of the witch hazel water. It further serves the purpose as a smoothing agent and as an antiphlogistic.

THE SPANS AND THE TWEEN 80 (Polysorbate 80, U.S.P)

The nonionic surfactants have been used extensively in topical cosmetic and pharmaceuticals without evidence of irritation or sensitization. Tween 80 (Polysorbate 80 U.S.P.) serves as a detergent solution in place of soap.

SODIUM THIOSULFATE ((Sodium Hyposulfate)

Is added (synergistic) to other ingredients contained in the lotion. Because of its keratolytic effect it tends to soften skin, thus, permitting the active ingredients to penetrate into the dermis.

TRAGACANTH U.S.P.

Is obtained by incising the shrubs of Atragalus species growing in Asiatic countries. It contains from 60 percent to 70 percent of a complex substance called bassorin 30 to 40 percent of a constituent called tragachinthin. It is used as a suspending medium in the lotion and by its use in the lotion leaves a smooth homogenous film on the face.

The lotion is applied to the skin in an amount sufficient to form a stable film on the skin. For instance, the lotion may be applied to the face of a person in an amount of about 4 ml. of lotion or about a teaspoon for the entire face or about 2.5 grams. This should be repeated at least twice a day. Additional applications are made to the extent necessary to maintain the existence of a film. In certain cases, hourly applications or applications every other hour is recommended.

INDICATIONS FOR FORMULA

1. Detergent moisturizing topical lotion and astringent to be applied to the skin and other areas of the body (e.g., the scalp) leaving the skin soft with a smoothness like a baby's skin.
  a. as a acceptable cosmetic for teenagers and all ages
  b. for men either before of after shaving
2. For the improvement of seborrheic capitis (dandruff of the scalp)
3. For the prevention and to expedite involuting of herpes simples (Type I) cracks and fissures of the skin (E/g Perleche) and mucous membranes of the oral cavity
4. For a perfectly smooth skin when used the night before shaving (for men).
5. As a smooth skin devoid of blemishes—When used once or twice daily the skin feels just like a baby's skin.

Without further elaboration, the foregoing will so fully illustrate my invention that others may, by applying current to future knowledge, adopt the same for use under various conditions of service.

I claim:

1. A novel skin lotion comprising the following ingredients:

| | |
|---|---|
| Menthol | 24 gm. |
| Allantoin | 120 gm. |
| Castor Oil | 250 ml |
| Oleic Acid | 100 ml |
| Span 80 | 120 ml |
| Span 85 | 120 ml |
| Tween 80 | 120 ml |
| Span 40 | 120 ml |
| Borax | 10 |
| Sodium Thiosulfate | 48 gm. |
| Tragacanth | 88 gm. |
| Calcium Hydroxide Powder | 1750 ml |
| Witch Hazel Water | 4000 ml |

2. The novel skin lotion of claim 1, including the addition of fragrance.

3. The lotion of claim 1, wherein the novel skin lotion is a moisturizer used prior to shaving.

* * * * *